(12) United States Patent
He et al.

(10) Patent No.: US 12,140,580 B2
(45) Date of Patent: Nov. 12, 2024

(54) ESTIMATION METHODS FOR CARBON STOCKS IN COASTAL ECOSYSTEMS

(71) Applicant: NANJING INSTITUTE OF ENVIRONMENTAL SCIENCES, MINISTRY OF ECOLOGY AND ENVIRONMENT OF THE P.R.C., Nanjing (CN)

(72) Inventors: Fei He, Nanjing (CN); Weixin Li, Nanjing (CN); Jie Ma, Nanjing (CN); Han Qiu, Nanjing (CN); Zhuang Liu, Nanjing (CN); Yufeng Xie, Nanjing (CN); Jian Li, Nanjing (CN); Xuhan Zhang, Nanjing (CN); Jianhui Liu, Nanjing (CN); Chao Fu, Nanjing (CN)

(73) Assignee: NANJING INSTITUTE OF ENVIRONMENTAL SCIENCES, MINISTRY OF ECOLOGY AND ENVIRONMENT OF THE P.R.C, Nanjing (CN)

( * ) Notice: Subject to any disclaimer, the term of this patent is extended or adjusted under 35 U.S.C. 154(b) by 344 days.

(21) Appl. No.: 17/743,912

(22) Filed: May 13, 2022

(65) Prior Publication Data

US 2023/0118669 A1 Apr. 20, 2023

(30) Foreign Application Priority Data

Oct. 15, 2021 (CN) .......................... 202111200918.7

(51) Int. Cl.
*G01N 33/00* (2006.01)
*G01N 33/24* (2006.01)
(Continued)

(52) U.S. Cl.
CPC ......... *G01N 33/0098* (2013.01); *G01N 33/24* (2013.01); *G06F 16/906* (2019.01); *G06Q 50/26* (2013.01); *Y02P 90/84* (2015.11)

(58) Field of Classification Search
USPC ............................................................ 702/2
See application file for complete search history.

(56) References Cited

U.S. PATENT DOCUMENTS

| 2018/0267205 | A1* | 9/2018 | Harris | ..................... G01V 20/00 |
| 2022/0307958 | A1* | 9/2022 | Chen | ..................... G01N 33/24 |
| 2022/0324737 | A1* | 10/2022 | Ozair | ....................... C02F 9/20 |

FOREIGN PATENT DOCUMENTS

| CN | 103345573 A | 10/2013 |
| CN | 109669022 A | 4/2019 |

(Continued)

*Primary Examiner* — Paul D Lee
(74) *Attorney, Agent, or Firm* — Birch, Stewart, Kolasch & Birch, LLP

(57) ABSTRACT

The coastal ecosystem carbon pool estimation method of the invention belongs to the field of environmental assessment, and includes the following steps: (a) determining the spatial boundary of the coastal ecosystem; (b) determining the dominant plant classification area of the coastal ecosystem; (c) calculating the carbon source of the freshwater plant dominant area; (d) size setting of carbon source sampling point in coastal ecosystem; (e) sampling method of carbon source sampling point in coastal ecosystem; (f) carbon source estimation method in coastal ecosystem. The beneficial effects of the invention are as follows: a new method for classifying vegetation areas in coastal ecosystems by using dominant species is proposed, which reduces the difficulty of sampling and simplifies sampling steps; proposes a boundary division method for water body communication and carbon source calculation The method effectively fills the gap of the carbon source survey method in the estuary area; the proposed specific carbon source calculation method for (Continued)

tall shrubs and trees greatly reduces the difficulty and workload of the survey.

4 Claims, 3 Drawing Sheets

(51) Int. Cl.
*G06F 16/906* (2019.01)
*G06Q 50/26* (2012.01)

(56) References Cited

FOREIGN PATENT DOCUMENTS

| | | |
|---|---|---|
| CN | 110032611 A | 7/2019 |
| CN | 112182474 A | 1/2021 |
| CN | 112183154 A | 1/2021 |
| CN | 113888383 A | 1/2022 |

* cited by examiner

ESTIMATION METHODS FOR CARBON STOCKS IN COASTAL ECOSYSTEMS

TECHNICAL FIELD

The invention belongs to the technical field of environmental assessment and in particular, relates to a method for estimating carbon storage in coastal ecosystems.

BACKGROUND TECHNIQUE

Typical coastal ecosystems generally include three common plant types: coastal trees and tall shrubs, tidal salt marshes, and seagrass beds. These three plant types enable coastal ecosystems to withstand storm surges, slow sea-level rise and reduce coastal erosion. Due to the growth, reproduction and death of plants themselves, coastal ecosystems also have ecological and environmental functions such as carbon sequestration, water quality regulation, nutrient capture, and habitat provision for organisms.

Due to the rich plant species and considerable reserves in the coastal plant belt, the role of coastal ecosystems in carbon sequestration is very significant. If it is degraded, it will become a severe source of carbon emissions. There is no relatively complete method for estimating carbon storage in coastal ecosystems. Feasible and fairly accurate carbon stock estimates are the scientific basis for establishing carbon financing mechanisms for coastal ecosystems.

SUMMARY OF THE INVENTION

The present invention's aim is to provide a method for estimating carbon stocks in coastal ecosystems to reduce or avoid the problems above.

In order to solve the above problems, the present invention provides a method for estimating carbon stocks in coastal ecosystems, which comprises the following steps:
(a) Spatial boundary determination of coastal ecosystems.
(b) Determination of dominant plants in different areas of coastal ecosystems.
(c) Calculation of carbon stocks in freshwater plant dominant areas.
(d) Size setting of carbon source sampling points in coastal ecosystems.
(e) Sampling methods for carbon source sampling points in coastal ecosystems.
(f) Carbon stocks estimation methods for coastal ecosystems.

Theoretically, the spatial boundary used for carbon stocks estimation can range from tens of hectares to hundreds of square kilometers. The commonly considered methods are: physical boundary division; administrative boundary division and biological boundary division. The present invention proposes a new boundary division method: a boundary division method based on water body communication, which belongs to a physical boundary division method.

Spatial boundary determination of coastal ecosystems in the step (a) specifically includes the following content:
(a1) For non-estuarine areas: take the intertidal zone as the core area, extend to the lowest tide level in history, and extend to the shore direction where soil salinity is lower than 5% of the seawater salinity.
(a2) For the estuary area, specifically, for the longitudinal length of the estuary, the width of the intertidal zone plus two times the width of the riparian zone is used. For the lateral distance of the estuary involved in the calculation, two times the riparian width is used. The above-mentioned riparian zone width refers to the width between the highest water level and the lowest water level of the river;

After repeated on-site investigations and comparative analysis, the inventor found that by using the above boundary division method, coastal ecosystems can be classified according to the spatial organization, avoiding the roughness of physical boundary division and the unreasonable administrative boundary division. Supportive and creatively reduce the difficulty for investigators to use biological boundaries. The resulting carbon stock estimates did not differ significantly from the full-area survey using the biological boundary division method.

Methods for determining dominant plant species in different coastal ecosystems: traditionally, it is necessary to identify dominant plant species and divide the area of mixed species according to different plant proportions. When a species occupies the majority area of the area, it is identified as this species is the dominant species, and the area occupied by it needs to be measured, while the area occupied by other non-dominant species also needs to be recorded.

In the above-mentioned step (b) of the present invention, the method for determining the dominant plant species specially used for calculating the carbon stocks is:

The plant species in coastal ecosystems are divided into three types: coastal trees and tall shrubs; tidal salt marshes; and seagrass beds; and all other plants are classified into these three types. The shrubs or trees, which height exceeds 1.2 m are classified as coastal trees, those less than 1.2 m and higher than 0.1 m are classified as tidal salt marshes, and those less than 0.1 m are classified as seagrass bed plants. The $CO_2$ equivalent is 0.01415 kg/m² for coastal trees, 0.00935 kg/m² for tidal salt marshes, and 0.00396 kg/m² for seagrass beds.

If the estimated coastal ecosystem includes an estuary area, it is classified into a single plant-dominant area, which is named as a freshwater plant dominant area because its main carbon source is fluvial carbon.

In the above step (c) of the present invention, the calculation of carbon source in the freshwater plant dominant area, the specific method is:
(c1) In the flood season, use the suspended sediments sampling method to sample the freshwater plant dominant area, dry the samples, and obtain the organic matter then calculate the carbon weight $W_c$ in each cubic meter of water, unit: kg/m³.

The suspended sediments sampling method is: using the sampling buckets to obtain samples from a cross-section of the river, the sampling points are evenly distributed in the cross-section.
(c2) The annual carbon dioxide equivalent is calculated from the river flow, and the specific calculation method is as follows:

$$W_{yc} = 3.670 W_c \times W$$

In which, W is the total annual runoff of the river (m³), and $W_{yc}$ is the annual input carbon dioxide equivalent of the river (kg), $W_c$ is the carbon weight per cubic meter (kg/m³).

In the above step (d) of the present invention, the carbon source sampling point size setting of the coastal ecosystem, the specific setting method is as follows:
(d1) Do not arrange any sampling points for the freshwater plant dominant area.
(d2) The arrangement of sampling points for coastal trees is as follows:
For coastal trees type areas, use a side length of 50 m×50 m as the sampling unit.

(d3) The arrangement of sampling points for tidal salt marshes is as follows:

For tidal salt marsh type, use a side length of 1 m×1 m as the sampling unit.

(d4) The arrangement of sampling points for seagrass beds is as follows:

An area defined as a seagrass bed type was selected, and a 1 m×1 m area was used as the sampling unit.

In the above step (e) of the present invention, the sampling method of carbon source sampling point of the coastal ecosystem is:

(e1) The sampling methods for coastal trees are as follows:

Measure the diameter D at breast height (DBH) of all coastal trees in the sampling unit, and the height of the trunk H, select the plant with the largest diameter at breast height, use a laser scanner to measure and calculate the appearance size of the crown of the largest plant, and integrate to obtain its crown volume V, and calculate its biological amount, converted to carbon.

(e2) The following sampling methods were adopted for the tidal salt marsh sampling points:

There are two main plant groups in tidal salt marshes: low shrubs and terrestrial herbs. Due to their mixed planting status, it is difficult to clearly classify them. After years of on-site investigation and calculation, the inventor proposed the following methods to sample them:

All the living plants above the soil are cut down, dried and weighed, and used to calculate the carbon content of the above-ground part.

Take the tidal salt marsh soil with a depth of 1 m and a length and width of 1 m, 1) cleaning to obtain all the root systems; 2) carrying out specific gravity sieving on the cleaned mixed solution, and sieving out the part that obviously belongs to sediment and inorganic calcium, retain the humus and organic matter, and put the humus and organic matter into the transport sampling tank; 3) weigh the sieved sandy part and wash it with dilute hydrochloric acid, weigh the washed weight, and calculate the amount of carbon in the washed calcium carbonate, recharge all sandy parts into the sampling pit.

(e3) For seagrass beds, use the following sampling methods:

Mow all the live seagrass on the sampling square of the seagrass bed, bring it back to the lab test, dry and weigh it, and calculate its carbon content.

A Luoyang shovel sampler with a cross-sectional area of 0.01 m² was used to obtain soils with a depth of 1 m in each of the four corners and the center of the sample unit. When the soil depth of the plot was less than 1 m, the actual depth was recorded.

When the sample was brought back to the test, the carbon content was obtained by water washing and acid washing.

The carbon source estimation methods of coastal ecosystems in the above step (f), include the following:

(f1) For coastal trees, the calculation formula is as follows:

The formula for calculating the dry weight of the trunk biomass is: $B_s = 830 \times D_{max}^{1.92} H_{avg}$ The calculation formula of canopy biomass is: $B_c = 3.497 \times V$ $W_{crown} = B_c \times 0.454$;

$W_{trunk} = B_s \times 0.465$;

$W_{root} = 2.67 S_{crown}$;

$W_c = W_{crown} + W_{trunk} + W_{root}$

The carbon dioxide equivalent of all live plants in the plot is:

$W_{cs} = n \times (D_{avg}/D_{max}) \times W_c$

Among them, n is the number of plants in the plot, $D_{avg}$ is the average diameter of all plants in the plot, and $D_{max}$ is the maximum DBH in the plot.

The soil of 1 m×1 m×1 m in each of the four corners of the sampling square was burned, and the carbon content was measured and averaged to represent the soil carbon content in the sample square.

Through repeated tests and comparisons, the inventor found that in the coastal forest belt composed of tall shrubs and trees, using the thickest plant in a quadratic as a representative, the error between carbon content statistics and reality is small, and the sample is greatly reduced. Statistical workload. In particular, the use of the coefficient between the crown and the root system to calculate the root carbon content completely solves the complex problem of the root carbon content of living plants, which is accurate and efficient.

(f2) For the carbon source of tidal salt marsh plant types, the calculation formula is as follows:

All the living plants above the soil were cut down, dried and weighed, and used to calculate the carbon content of the above-ground part, for the underwater part, the carbon content of organic matter and the inorganic matter was measured by water washing and acid washing respectively.

After repeated sampling, measurement and calculation, the inventor found that the main carbon sources in tidal salt marshes are the carbon in the underground root system and humus organic matter. Moreover, the carbon source data of one sampling square can represent a large area with similar vegetation distribution, and the represented area is obviously distributed in strips along the coastline.

(f3) For seagrass bed type carbon source, the calculation method is as follows:

For the part above the seabed, it is dried and weighed, and its carbon content is obtained by the burning method.

For the part below the seabed, the sample was washed with water to obtain its carbon content by the burning method, and the carbon content of the part below the seabed in the quadrature was converted.

(f4) Calculate the amount of carbon in the entire survey area.

The beneficial effects of the present invention are:

1. The invention proposes a method for classifying vegetation areas in a coastal ecosystem by using dominant species, which reduces the sampling difficulty and simplifies the sampling steps.
2. The invention proposes a boundary division method for water body communication, which effectively fills the blank of the method for investigating carbon sources in estuary areas.
3. The specific carbon source calculation method for tall shrubs and trees proposed in the present invention greatly reduces the difficulty and workload of investigation.

DESCRIPTION OF DRAWINGS

The following drawings are only intended to illustrate and explain the present invention schematically and do not limit the scope of the present invention. Wherein.

DETAILED DESCRIPTION

The present invention will be further described below with reference to specific embodiments, but the protection scope of the present invention is not limited thereto.

Example 1

Figure 1:
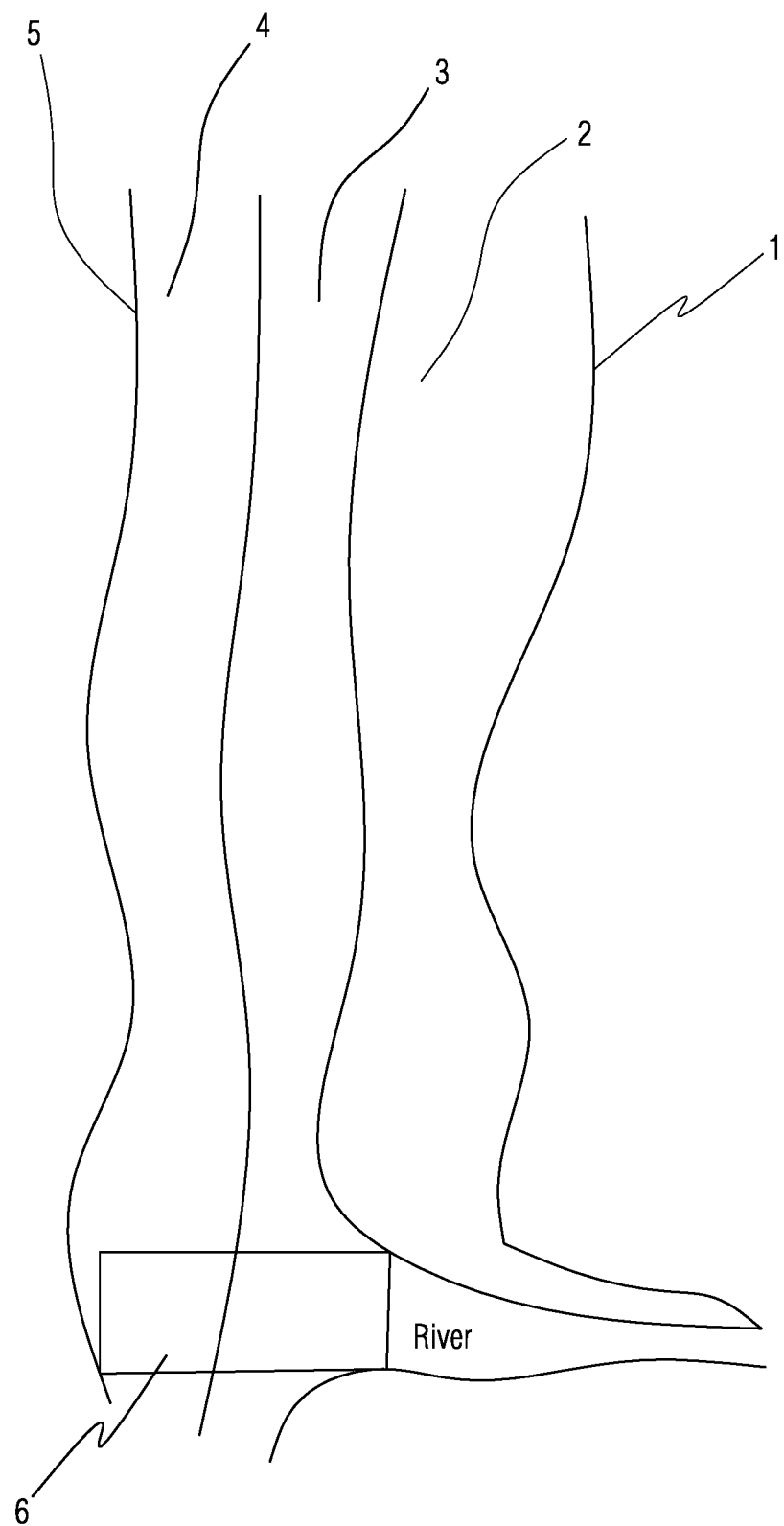
FIG. 1 is the survey area determination schematic diagram of the present invention.

As shown in FIG. 1, Estimate carbon stocks in the project area, including the following steps:
- (a) Boundary division method based on water connectivity.
- (a1) For non-estuarine area: take the intertidal zone as the core area, extend to the historical minimum tide level in the sea direction, and extend to the salinity contour boundary 1 with soil salinity of 5% of seawater salinity in the shore direction.
- (a2) Estuary area of this project: the width of the intertidal zone of this project is 1500 m, and the width of the riparian zone on both sides is 267 m and 304 m respectively, then the longitudinal length of the estuary is 1500+333+267=2100 m, and the lateral width is extended to the top of both riparian zones.
- (b) Determination of dominant plant taxonomic areas in coastal ecosystems.

The dominant plant classification area of the coastal ecosystem is determined, the dominant plants in this project grow along the coastal zone, as shown in FIG. 1, the area of the coastal tree 2, the tidal salt marsh area 3, the seagrass bed area 4, the historical lowest tide level is 5, and the freshwater plant predominant area is 6.

The plant species in coastal ecosystems are divided into three types: coastal trees and tall shrubs; tidal salt marshes; and seagrass beds; and all other plants are classified into these three types. The shrubs or trees whose height exceeds 1.2 m are classified as coastal trees, those less than 1.2 m and higher than 0.1 m is classified as tidal salt marshes, and those less than 0.1 m are classified as seagrass bed plants.

There is no other data to support this example, and the following data are used to calculate the carbon dioxide equivalent:

The carbon dioxide equivalent of coastal trees was 0.01415 kg/m², the carbon dioxide equivalent of tidal salt marshes was 0.00935 kg/m², and the carbon dioxide equivalent of seagrass beds was 0.00396 kg/m².

If the estimated coastal ecosystem includes an estuary area, it is divided into a plant-dominant area, which is called a freshwater plant-dominant area because its main carbon source is from river sediments.

The carbon dioxide equivalent of the freshwater plant dominant area is divided by the width of the estuary area along the river width:

The calculation method of the width along the river lateral direction is: river lateral direction width=minimum water level river width at the lowest tide level+left bank riparian width+right bank riparian width.

When the width of the river in the lateral direction is ≥5 km, the carbon dioxide equivalent in the estuary area is 0.00287 kg/m².

When the width of the river in the lateral direction is 5 km>1.5 km, the carbon dioxide equivalent in the estuary area is 0.00307 kg/m².

When the width of the river in the lateral direction is less than 1.5 km, the carbon dioxide equivalent in the estuary area is 0.00162 kg/m².

In this example, the freshwater plant's dominant area's river width is 1.47 km and less than 1.5 km, so its carbon dioxide equivalent is 0.00162 kg/m².

TABLE 1

The area occupied by each species in this project and the calculation of carbon dioxide equivalent

| Species of plant | Tall Shrubs and Coastal Trees | tidal salt marsh | seagrass bed | Predominant area of freshwater plants |
|---|---|---|---|---|
| area (m²) | 11711816.9 | 7492114.1 | 8656433.5 | 2148945.5 |
| carbon dioxide equivalent(kg) | 165722.21 | 70051.27 | 34279.48 | 3481.29 |

Total estimated regional $CO_2$ equivalents for this project (kg) 273534.2

Example 2

Estimate Carbon Stocks in the Project Area:

The step (a) and step (b) is the same as in Example 1. For different plant species classification areas in the ecosystem, the carbon amount is estimated by the following method instead of using the fixed value of Example 1.
- (c) Calculation of carbon sources in freshwater plant dominant areas.

The specific calculation method is:
- (c1) In the flood season, use the suspended sediments sampling method to sample the freshwater plant dominant area with suspended sediments sample device, dry the samples, obtain the organic matter then calculate the carbon weight $W_c$ in each cubic meter of water, unit: kg/m³; $W_c$=0.00027 kg/m³.
- (c2) The annual carbon dioxide equivalent is calculated from the river flow, and the specific calculation method is as follows:

$$W_{yc}=3.67 \times 0.00027 \times 56.1 \times 10^9 = 55589.49 (T/a)$$

In which, W=56.1×10⁹ m³ is the total annual runoff of the river, and $W_{yc}$ is the annual input carbon dioxide equivalent of the river.

Example 3

- (d) Size setting of carbon source sampling points in coastal ecosystems.

The carbon source sampling point size setting of the coastal ecosystem, the specific setting method is as follows:
- (d2) The arrangement of sampling points 21 for coastal trees is as follows:

Areas defined as coastal trees were selected, with a side length of 50 m×50 m unit to divide the area.
- (d3) The arrangement of sampling points for tidal salt marshes is as follows:

Select an area defined as a tidal salt marsh type, and use a side length of 1 m×1 m unit to divide the area.
- (d4) The arrangement of sampling points for seagrass beds is as follows:

An area defined as a seagrass bed type was selected, and a 1 m×1 m unit was used to divide the area.

Sampling methods for carbon source sampling points in coastal ecosystems.

Figure 2:
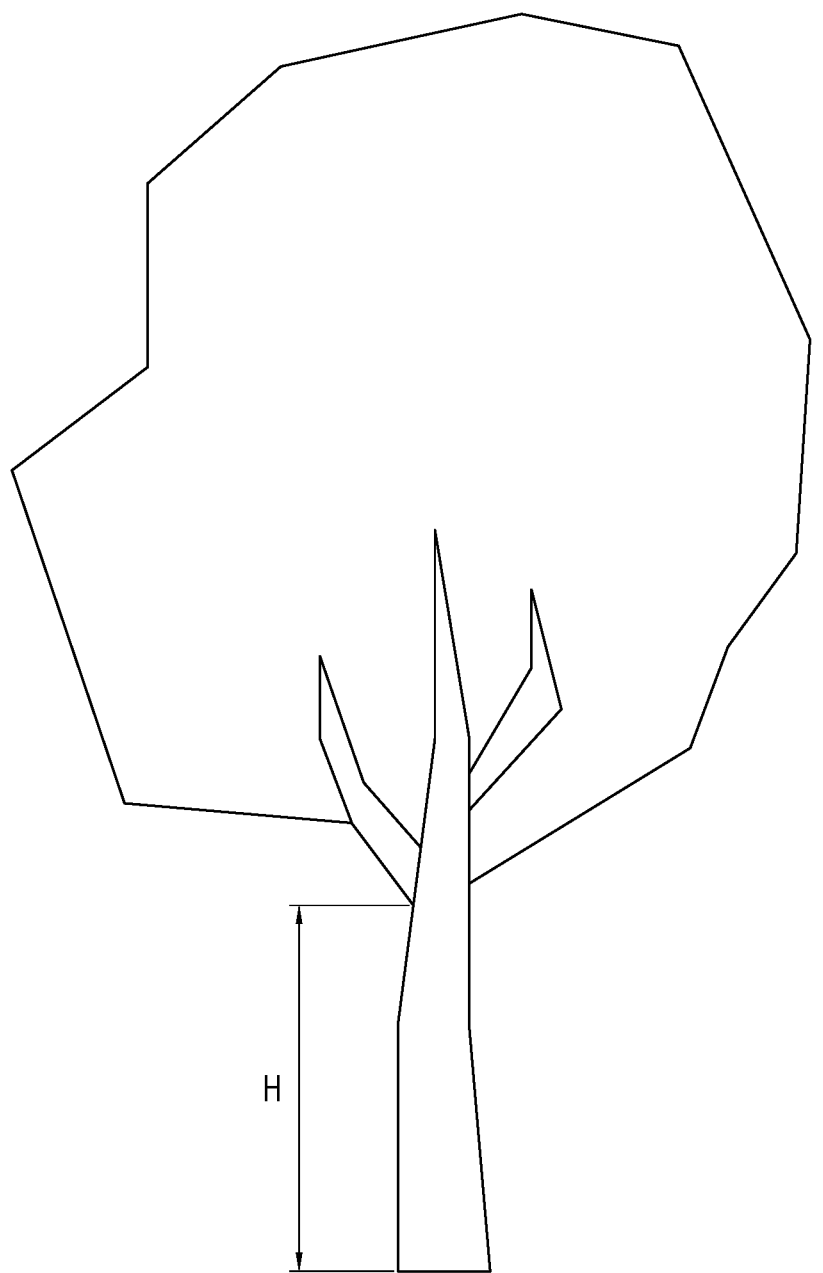
FIG. 2 is a schematic diagram of the strip-shaped distribution of the investigation area of the present invention.
Figure 3:
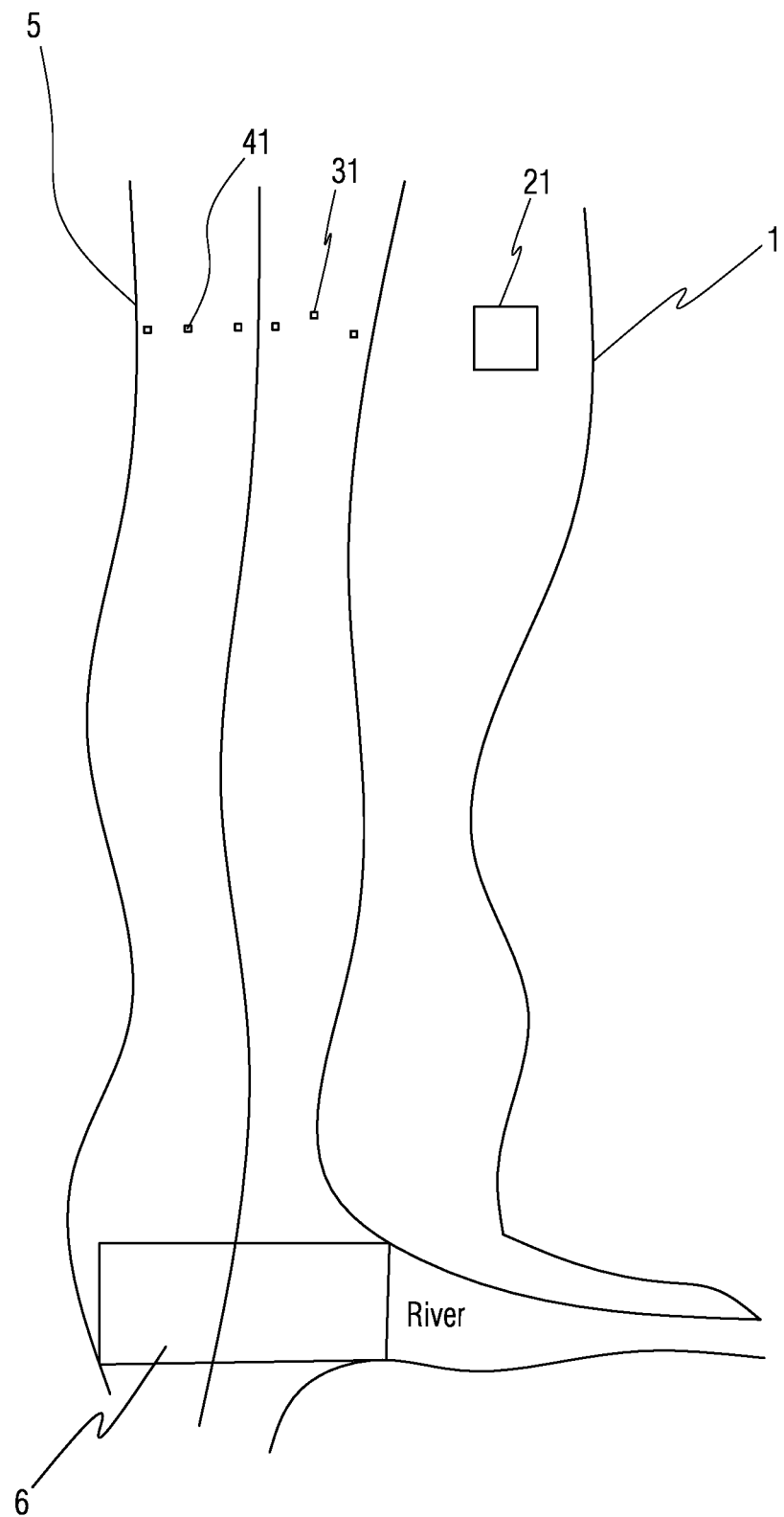
FIG. 3 is a schematic diagram of the tall shrubs and trees quadrat, tidal salt marsh plant quadrat and seagrass bed type quadrat in the survey area of the present invention.

In the above step (e), the sampling method of carbon source sampling point of the coastal ecosystem is:

(e1) The sampling methods for coastal trees are as follows:

Measure the DBH and trunk height H of all coastal trees in the sampling unit, see Table 2, select the plant with the largest DBH, and use a laser scanner to measure and calculate the canopy volume V of the largest plant, see FIG. 2. Calculate its biomass and convert to carbon equivalent; the diameter at breast height used here is the diameter of 1.3 m above the ground. The trunk height here is the height from the ground to the top of the tree.

TABLE 2

Diameter at breast height and trunk height of coastal trees in the sampling unit

| No. | D (m) | H (m) |
|---|---|---|
| 1 | 0.080 | 1.25 |
| 2 | 0.115 | 1.36 |
| 3 | 0.134 | 1.42 |
| 4 | 0.169 | 1.53 |
| 5 | 0.067 | 1.59 |
| 6 | 0.073 | 1.32 |
| 7 | 0.143 | 1.45 |
| 8 | 0.080 | 1.25 |
| 9 | 0.115 | 1.36 |
| 10 | 0.045 | 1.28 |
| 11 | 0.080 | 1.25 |
| 12 | 0.108 | 1.34 |
| 13 | 0.111 | 1.35 |
| 14 | 0.089 | 1.28 |
| 15 | 0.118 | 1.37 |
| 16 | 0.153 | 1.48 |
| 17 | 0.092 | 1.29 |
| 18 | 0.083 | 1.26 |
| 19 | 0.076 | 1.44 |
| 20 | 0.048 | 1.52 |
| 21 | 0.089 | 1.28 |

Th tree with the largest diameter at breast height in the above table is No. 4, the diameter at breast height is 0.169 m, and the trunk height is 1.53 m. The appearance size of the crown is measured with a laser scanner, and the crown volume V=5.03 m$^3$.

In step (f), the carbon source estimation methods for the above six coastal ecosystems include the following:

(f1) For coastal trees, the calculation formula is as follows:

The formula for calculating the dry biomass of the canopy is: $B_c=3.497 \times V=17.59$ (kg)

The formula for calculating the dry weight of the trunk biomass is: $B_s=830 \times D_{max}^{1.92} H_{avg}=830 \times 0.169^{1.92} \times 1.37=28.5$ (kg)

$W_{crown}=B_c \times 0.454=17.59 \times 0.454=7.98$ kg;

$W_{trunk}=B_s \times 0.465=28.5 \times 0.465=13.25$ kg $W_{root}=2.67 S_{crown}=2.67 \times 7.98=21.32$ kg;

$W_c=W_{crown}+W_{trunk}+W_{root}=7.98+13.25+21.32=42.56$ kg $D_{max}$ is the maximum diameter at breast height in the plot, and $H_{avg}$ is the average plant height in the sampling unit.

The carbon dioxide equivalent of all live plants in the plot is:

$W_{cs}=n \times (D_{avg}/D_{max}) \times W_c$ $W_{cs}=21 \times (0.098/0.169) \times 42.56=518$ kg In which, n is the number of plants in the plot, $D_{avg}$ is the average diameter of all plants in the sampling unit, and $D_{max}$ is the maximum DBH in the sampling unit.

Through repeated tests and comparisons, the inventor found that in the coastal forest belt composed of tall shrubs and trees, using the thickest plant in a quadratic as a representative, the error between carbon content statistics and reality are small. The sample is small is greatly reduced statistical workload. In particular, the coefficient between the crown and the root system to calculate the root carbon content completely solves the complex problem of the root carbon content of living plants, which is accurate and efficient.

The carbon dioxide equivalent conversion formula for the dry weight of plants in this sample square is:

To calculate the canopy volume, the $CO^2$ equivalent of the crown was calculated using the $CO^2$ equivalent parameter of 0.454, and the $CO^2$ equivalent of the trunk was calculated using the parameter 0.465. The total $CO^2$ equivalent of the roots and surrounding humus soil was 2.67 times the $CO^2$ equivalent of the crown.

In this example, the tall shrub and coastal tree type area are 11711816.9 m$^2$, and the carbon dioxide equivalent of the tall shrub is 2426688.5 kg.

Example 4

(e2) The following sampling methods are adopted for the tidal salt marsh sampling points 31:

There are two main plant groups in tidal salt marshes: low shrubs and terrestrial herbs. Due to their mixed planting status, it is difficult to classify them clearly. After years of on-site investigation and calculation, the inventor proposed the following methods to sample them:

All the live plants above the plot's soil were cut down, dried and weighed to obtain a total weight of 3.2 kg of dry matter, where the unit is 1 m$^2$. The carbon dioxide equivalent obtained by the combustion method is 1.28 kg, and the carbon dioxide equivalent parameter of the mixed dry matter of the tidal salt marsh surface vegetation is 1.28 kg/m$^2$.

Take the tidal salt marsh soil with a depth of 1 m and a length and width of 1 m, 1) cleaning to obtain all the root systems therein; 2) carrying out specific gravity sieving on the cleaned mixed solution, and sieving out the part belonging to sediment and inorganic calcium, retain the humus and organic matter and put the humus and organic matter into the transport sampling tank; 3) weigh the sieved sandy part and wash it with dilute hydrochloric acid, weigh the washed weight, and calculate the amount of carbon in the washed calcium carbonate, recharge all sandy parts into the sampling pit.

The total weight of humus and organic matter obtained after cleaning the root system is 5.92 kg; the carbon dioxide weight obtained by burning is 2.37 kg.

The amount of carbon dioxide obtained was 0.18 kg.

In this way, the carbon dioxide equivalent parameter of the tidal salt marsh sampling point is $W_{salt\ marsh}=W_{above\ ground\ part}+W_{underground\ part}+W_{calcium\ carbonate}=1.28+2.37+0.18=3.83$ kg/m$^2$.

In this example, the area of the tidal salt marsh area is 7492114.1 m$^2$, and the carbon dioxide equivalent of the tidal salt marsh area is calculated to be 28694797 kg.

Example 5

(e3) For the seagrass bed sampling point 41, the following sampling methods are adopted:

Mow all the live seagrass on the sampling square of the seagrass bed, take it back to the laboratory, dry it and weigh it.

A Luoyang shovel sampler with a cross-sectional area of 0.01 m² was used to obtain soils with a depth of 1 m in each of the four corners and the unit's centre. When the soil depth of the unit was less than 1 m, the actual depth was recorded. Take it back to the laboratory for washing and drying.

The carbon dioxide equivalent of the sample was measured by the combustion method of the above organic matter.

The carbon dioxide equivalent obtained in the quadrat of this example is 0.034 kg/m³, and the carbon dioxide equivalent of the seagrass bed in the survey area is 294318.7 kg.

The carbon dioxide equivalent of the entire survey area is calculated as follows: the annual carbon dioxide equivalent of the river: is 55589490 kg+the carbon dioxide equivalent of tall shrubs is 2426688.5 kg+the carbon dioxide equivalent of the tidal salt marsh area is 28694797 kg+the carbon dioxide equivalent of the seagrass bed is 294318.7 kg=87005 T.

While the present invention has been explained by reference to the examples of preferred embodiments described above, it will be appreciated that those are examples to assist in understanding the present invention and are not meant to be restrictive. Variations or modifications that are obvious or trivial to persons skilled in the art and improvements made thereon should be considered equivalents of the invention.

The invention claimed is:

1. A method for estimating an amount of carbon sources in coastal ecosystems comprising the following steps:
  a step (a) of determining a spatial boundary of the coastal ecosystems including non-estuarine areas and an estuary area, comprising the substeps of;
    (a1) defining the non-estuarine areas by taking an intertidal zone as a core area, extending to a lowest tide level in history in a sea, and extending to a shore to the extent that a soil salinity is lower than 5% of a sea water salinity;
    (a2) defining the estuary area by including a space between the intertidal zone and a riparian zone, using a width of the intertidal zone plus 2 times a width of the riparian zone as a longitudinal length of the estuary area, and using 2 times the width of the riparian zone as a lateral distance of the estuary area, wherein the width of the riparian zone is a width between a highest water level and a lowest water level of a river;
  a step (b) of determining dominant plant taxonomic areas in the coastal ecosystems;
  a step (c) of calculating an amount of carbon sources in freshwater plant dominant areas;
  a step (d) of setting size of carbon source sampling points in the coastal ecosystems;
  a step (e) of carrying out sampling methods for the carbon source sampling points in the coastal ecosystems; and
  a step (f) of calculating a total amount of carbon sources in the coastal ecosystems,
  wherein the step (c) comprises the substeps of:
    (c1) in a flood season, using a suspended sediments sampling method to sample the freshwater plant dominant area, drying the samples, obtaining an organic matter, and calculating a carbon dioxide weight We in each cubic meter of water, having a unit of kg/m³; and
    (c2) calculating an annual carbon dioxide equivalent from a river flow according to:

$$W_{yc} = 3.670 W_c \times W,$$

wherein W is a total annual runoff of the river (m³), and $W_{yc}$ is an annual input carbon dioxide equivalent of the river (kg).

2. The method for estimating an amount of carbon sources in coastal ecosystems according to claim 1, wherein the step (b) further comprises:
  determining a dominant plant classification area of the coastal ecosystems;
  dividing plant species in the coastal ecosystems into:
    coastal trees and tall shrubs;
    tidal salt marshes; and
    seagrass beds,
  wherein shrubs or trees in coastal ecosystems with a height exceeding 1.2 m is classified as the coastal trees and tall shrubs, shrubs or trees in coastal ecosystems with a height less than 1.2, and higher than 0.1 m is classified as the tidal salt marshes, and shrubs or trees in coastal ecosystems with a height below 0.1 m is classified as the seagrass beds,
  wherein a carbon dioxide equivalent of the coastal trees and tall shrubs is 0.01415/m², a $CO_2$ equivalent of the tidal salt marshes is 0.00935/m², and a carbon dioxide equivalent of seagrass beds is 0.00396/m², and
  wherein the estuary area is classified into a single plant-dominant area, which is named as a freshwater plant dominant area.

3. The method for estimating an amount of carbon sources in coastal ecosystems according to claim 2, wherein the step (d) further comprises the substeps of:
  (d1) not arranging any sampling points for the freshwater plant dominant area;
  (d2) using a side length of 50 m×50 m as a sampling unit for areas of the coastal trees and tall shrubs;
  (d3) using a side length of 1 m×1 m as a sampling unit for areas of the tidal salt marshes; and
  (d4) using a 1 m×1 m area as a sampling unit for areas of the seagrass beds.

4. The method for estimating an amount of carbon sources in coastal ecosystems according to claim 3, wherein the step (e) further comprises the substeps of:
  (e1) for the coastal trees and tall shrubs:
  measuring a diameter D at breast height and a trunk height H for all coastal trees in the sampling unit, selecting a plant with a largest diameter at the breast height, using a laser scanner to measure and calculate an appearance size of a crown of the plant with the largest diameter at the breast height, obtaining a crown volume V of the plant with the largest diameter at the breast height, and calculating a biological amount according to the crown volume V, converted to carbon;
  (e2) for the tidal salt marshes:
  cutting down all living plants above the ground, drying and weight the living plants, and calculating a carbon content of the living plants; and
  obtaining a tidal salt marsh soil with a depth of 1 m and a length and width of 1 m, cleaning the tidal salt marsh soil to obtain all root systems in the tidal salt marsh soil, carrying out a gravity sieving on a cleaned mixed solution, sieving out a sandy part belonging to sediment and inorganic calcium, retaining a humus and organic matter, putting the humus and organic matter into a transport sampling tank, weighing the sieved sandy part and washing the sieved sandy part with dilute hydrochloric acid, weighing a washed weight, and calculating an amount of carbon in a washed calcium carbonate, and recharging all the sandy parts into the sampling unit;

(e3) for the seagrass beds:

mowing all live seagrass on the sampling unit, drying and weighting the live seagrass, and calculating a carbon content of the live seagrass;

using a Luoyang shovel sampler to obtain soils with a depth of 1 m in each of four corners and a center of the sampling unit, wherein when a soil depth of the sampling unit is less than 1 m, an actual depth is recorded, and when the soil depth of the sampling unit exceeds 1 m, a depth of 1 m is recorded; and obtaining a carbon content of the soils.

* * * * *